United States Patent

Shinoda

[11] Patent Number: 5,671,750
[45] Date of Patent: Sep. 30, 1997

[54] PERIPHERAL BLOOD-FLOW CONDITION MONITOR

[75] Inventor: Masayuki Shinoda, Tajimi, Japan

[73] Assignee: Colin Corporation, Komaki, Japan

[21] Appl. No.: 695,635

[22] Filed: Aug. 12, 1996

[30] Foreign Application Priority Data

Feb. 17, 1995 [JP] Japan ................ 7-29235

[51] Int. Cl.⁶ ........................... A61B 5/00
[52] U.S. Cl. .................. 128/672; 128/687; 128/691; 128/680
[58] Field of Search ................ 128/672, 687, 128/690, 691, 677, 680–3, 713

[56] References Cited

U.S. PATENT DOCUMENTS

| | | | |
|---|---|---|---|
| 5,101,828 | 4/1992 | Welkowitz et al. | 128/687 |
| 5,103,831 | 4/1992 | Niwa | 128/672 |
| 5,279,303 | 1/1994 | Kawamura et al. | 128/687 |
| 5,289,823 | 3/1994 | Eckerle | 128/672 |
| 5,293,874 | 3/1994 | Takahashi et al. | 128/691 |

FOREIGN PATENT DOCUMENTS

| | | |
|---|---|---|
| A-0 330 463 | 8/1989 | European Pat. Off. . |
| A-0 487 726 | 6/1992 | European Pat. Off. . |
| A-0 750 878 | 1/1997 | European Pat. Off. . |
| A-61-119239 | 6/1986 | Japan . |
| WO-A-96 22050 | 7/1996 | Japan . |

*Primary Examiner*—Robert L. Nasser, Jr.
*Attorney, Agent, or Firm*—Oliff & Berridge

[57] ABSTRACT

An apparatus for monitoring a peripheral blood-flow condition of a living subject by detecting a peripheral blood-flow resistance of the subject, including a first and a second pulse-wave sensor which are adapted to be worn on a first and a second portion of the subject, respectively, to detect a first and a second pulse wave, respectively, each of which is produced in synchronism with a heartbeat of the subject, a phase-difference determining device for determining a difference of respective phases of the first and second pulse waves detected by the first and second pulse-wave sensors, and a peripheral blood-flow resistance determining device for determining the peripheral blood-flow resistance of the subject, based on the phase difference determined by the phase-difference determining device, according to a predetermined relationship between peripheral blood-flow resistance and phase difference.

12 Claims, 7 Drawing Sheets

PERIPHERAL BLOOD-FLOW CONDITION MONITOR

BACKGROUND OF THE INVENTION

1. Field of the Invention

The present invention relates to a monitor which monitors peripheral blood-flow condition of a living subject by determining peripheral blood-flow resistance values of the subject.

2. Related Art Statement

A blood pressure (BP) monitor may be used to monitor BP values of a patient in an operation room or an intensive care unit (ICU). Even when the BP monitor reads accurate BP values of the patient, it is, however, not determinable whether the blood appropriately circulates or flows through the patient. Hence, a medical person such as a doctor or nurse may need to monitor peripheral blood-flow condition of the patient by touching a hand or a foot of the patient and judging whether the peripheral portion or tissue of the patient has an extremely low temperature.

Meanwhile, it has been proposed to measure BP values of a patient from each of his or her trunk and periphery portion and display respective time-wise trends of the two series of BP values, side by side, along a common time axis, so that a medical worker can quickly notice a possible significant change of the peripheral blood-flow condition of the patient. This technique is employed by a BP monitor disclosed in Japanese Patent Application filed by the Assignee of the present U.S. application and laid open for inspection purposes under Publication No. 61(1986)-119239.

The above-identified BP monitor requires the medical person to compare two curves representing the two time-wise BP trends with each other and qualitatively judge whether the peripheral blood-flow condition of the patient has significantly largely changed. However, only persons who are well familiar with the monitor device can make accurate judgments. In addition, the prior BP monitor does not provide any quantitative reading of the peripheral blood-flow condition of the patient. In particular, in the case where a patient under general anesthesia is monitored, his or her peripheral blood-flow condition may largely change due to the excitation of his or her nervous system, the administration of BP controlling agents, and/or his or her current body temperature. Therefore, the reading of quantitative values of the peripheral blood-flow condition of a patient is very important.

SUMMARY OF THE INVENTION

It is therefore an object of the present invention to provide a monitor which monitors, with accuracy, the peripheral blood-flow condition of a living subject by determining peripheral blood-flow resistance values of the subject.

The above object has been achieved by the present invention, which provides an apparatus for monitoring a peripheral blood-flow condition of a living subject by detecting a peripheral blood-flow resistance of the subject, comprising a first and a second pulse-wave sensor which are adapted to be worn on a first and a second portion of the subject, respectively, to detect a first and a second pulse wave, respectively, each of which is produced in synchronism with a heartbeat of the subject, phase-difference determining means for determining a difference of respective phases of the first and second pulse waves detected by the first and second pulse-wave sensors, and peripheral blood-flow resistance determining means for determining the peripheral blood-flow resistance of the subject, based on the phase difference determined by the phase-difference determining means, according to a predetermined relationship between peripheral blood-flow resistance and phase difference.

In the peripheral blood-flow condition monitor apparatus in accordance with the present invention, the peripheral blood-flow resistance determining means determines the peripheral blood-flow resistance of the subject, based on the phase difference determined by the phase-difference determining means, according to a predetermined relationship between peripheral blood-flow resistance and phase difference. The relationship may be predetermined based on experimental data, e.g., peripheral blood-flow resistance values and phase-difference values obtained from many people. The peripheral blood-flow resistance well reflects the peripheral blood-flow condition, such that higher peripheral blood-flow resistance values indicate worse peripheral blood-flow conditions and lower resistance values indicate better conditions. Thus, the present monitor apparatus monitors, with accuracy, the peripheral blood-flow condition of a living subject by determining the peripheral blood-flow resistance values of the subject.

According to a preferred feature of the present invention, the monitor apparatus further comprises a blood pressure measuring device which measures a blood pressure of the subject, and the peripheral blood-flow resistance determining means determines the peripheral blood-flow resistance of the subject, based on the phase difference determined by the phase-difference determining means and the blood pressure measured by the blood pressure measuring device, according to the predetermined relationship defined by a function of phase difference and blood pressure as variables. Since a mathematical function of phase difference and blood pressure as variables is used as the relationship for determining the peripheral blood-flow resistance values of the subject, the present monitor apparatus monitors, with higher accuracy, the peripheral blood-flow condition of the subject.

According to another feature of the present invention, the blood pressure measuring device comprises an inflatable cuff adapted to be wound around a body portion of the subject, and measuring means for measuring the blood pressure of the subject by changing a pressure of the cuff applied to the body portion of the subject, and the first pulse-wave sensor comprises the cuff, a pressure sensor which detects the pressure of the cuff, and a pulse-wave filter circuit which extracts, as the first pulse wave, an oscillatory pressure wave including a plurality of pulses produced in the cuff in synchronism with the heartbeat of the subject, from the cuff pressure detected by the pressure sensor. Since the cuff is used as not only a part of the blood pressure measuring means but also a part of the first pulse-wave sensor, the present monitor apparatus enjoys a simple construction.

According to another feature of the present invention, the monitor apparatus further comprises a cuff-pressure regulating device which increases the pressure of the cuff up to a predetermined value lower than a diastolic blood pressure of the subject and holds the cuff pressure at the predetermined value, and wherein the pulse-wave filter circuit extracts, as the first pulse wave, a plurality of heartbeat-synchronous pulses produced in the cuff held at the predetermined value, from the cuff pressure detected by the pressure sensor.

According to another feature of the present invention, the second pulse-wave sensor comprises a pressure pulse wave sensor which is adapted to be pressed against an artery of the subject via a skin of the subject, the pressure pulse wave sensor detecting, as the second pulse wave, a pressure pulse wave including a plurality of pulses produced from the artery of the subject in synchronism with the heartbeat of the subject. Each of the first and second pulse-wave sensor may otherwise be selected from the group consisting of an impedance-pulse-wave sensor which includes electrodes adapted to be held in contact with the surface of a body portion of a living subject and detects an impedance pulse wave as the change of impedance of the body portion; a supersonic-pulse-wave sensor which is held in contact with the surface of a body portion of a subject, emits supersonic wave toward an artery of the body portion via the surface, and detects, as a supersonic pulse wave, the displacement or vibration of the wall of the artery; or a photoelectric-pulse-wave sensor which is adapted to be worn on the surface of a body portion of a subject, emits light toward the body portion, and detects, as a photoelectric pulse wave, the light reflected from, or transmitted through, the body portion of the subject.

According to another feature of the present invention, the monitor apparatus further comprises index-value determining means for determining an index value indicative of a characteristic of a waveform of a decreasing portion of a heartbeat-synchronous pulse of the second pulse wave detected by the second pulse-wave sensor, wherein the peripheral blood-flow resistance determining means comprises correcting means for correcting, based on the index value determined by the index-value determining means, the peripheral blood-flow resistance determined based on the phase difference determined by the phase-difference determining means. Thus, the present monitor apparatus monitors, with higher accuracy, the peripheral blood-flow resistance condition of the subject.

According to another feature of the present invention, the monitor apparatus further comprises a display device which displays, along a time axis, a time-wise trend of respective values of the peripheral blood-flow resistance determined by the peripheral blood-flow resistance determining means. A medical person such as a doctor or nurse can easily notice a significant change of the peripheral blood-flow condition of the subject by viewing the screen image of the display device.

According to another feature of the present invention, the phase-difference determining means comprises means for determining a phase difference of each of heartbeat-synchronous pulses of the first pulse wave and a corresponding one of heartbeat-synchronous pulses of the second pulse wave, and wherein the peripheral blood-flow resistance determining means successively determines, according to the predetermined relationship, a peripheral blood-flow resistance of the subject, based on the phase difference of the each heartbeat-synchronous pulse of the first pulse wave and the corresponding heartbeat-synchronous pulse of the second pulse wave.

BRIEF DESCRIPTION OF THE DRAWINGS

The above and optional objects, features, and advantages of the present invention will better be understood by reading the following detailed description of the preferred embodiments of the invention when considered in conjunction with the accompanying drawings, in which.

DETAILED DESCRIPTION OF THE PREFERRED EMBODIMENTS

Referring to FIGS. 1 to 11, there will be described a blood pressure (BP) monitor 8 to which the present invention is applied. The BP monitor 8 may be used to monitor BP values of a patient who is undergoing, or has undergone, a surgical operation. The BP monitor also functions as a peripheral blood-flow condition monitor as described below.

Figure 1:
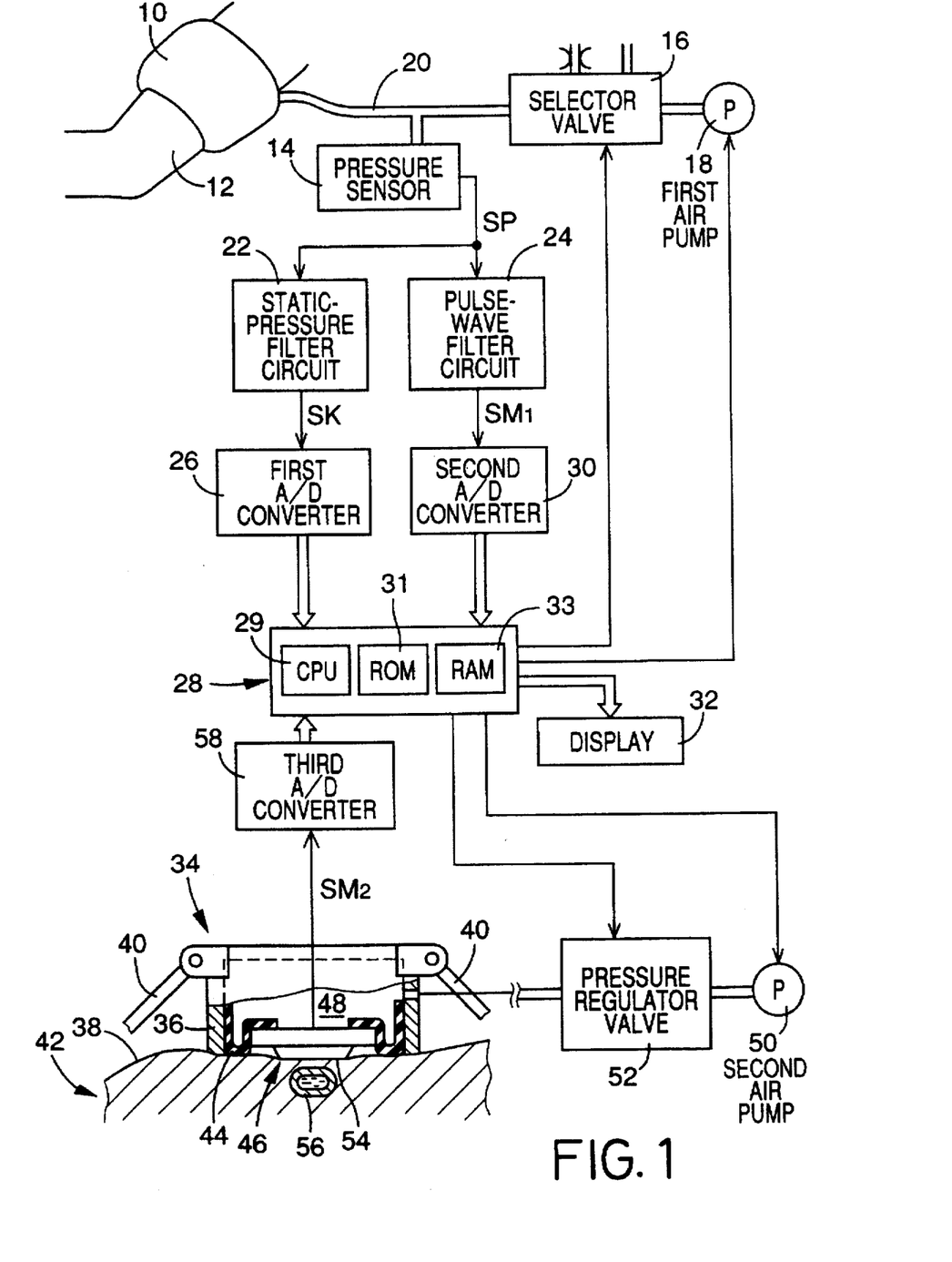
FIG. 1 is a diagrammatic view of a blood pressure (BP) monitor which also functions as a peripheral blood-flow condition monitor to which the present invention is applied.

In FIG. 1, the BP monitor 8 includes an inflatable cuff 10 including a rubber bag and a band-like cloth bag in which the rubber bag is accommodated. The cuff 10 is wound around, e.g., an upper arm 12 of a patient. The cuff 10 is connected via piping 20 to a pressure sensor 14, a selector valve 16, and a first air pump 18. The selector valve 16 is selectively placed, under control of an electronic control device 28, in a first state in which the valve 16 permits pressurized air to be supplied from the air pump 18 to the cuff 10 to increase quickly the air pressure of the cuff 10 (hereinafter, referred to as the "cuff pressure"), a second state in which the valve 16 causes the cuff 10 to be deflated slowly, and a third state in which the valve 16 causes the cuff 10 to be deflated quickly.

The pressure sensor 14 detects the cuff pressure (i.e., the air pressure of the cuff 10), and generates a pressure signal, SP, representing the detected cuff pressure. The pressure signal SP is supplied to each of a static-pressure filter circuit 22 and a pulse-wave filter circuit 24. The static-pressure filter circuit 22 includes a low-pass filter which extracts, from the pressure signal SP, a cuff-pressure signal, SK, representative of a static or direct-current component of the pressure signal SP. The cuff-pressure signal SK is supplied via a first analog-to-digital (A/D) converter 26 to the control device 28.

Figure 4:
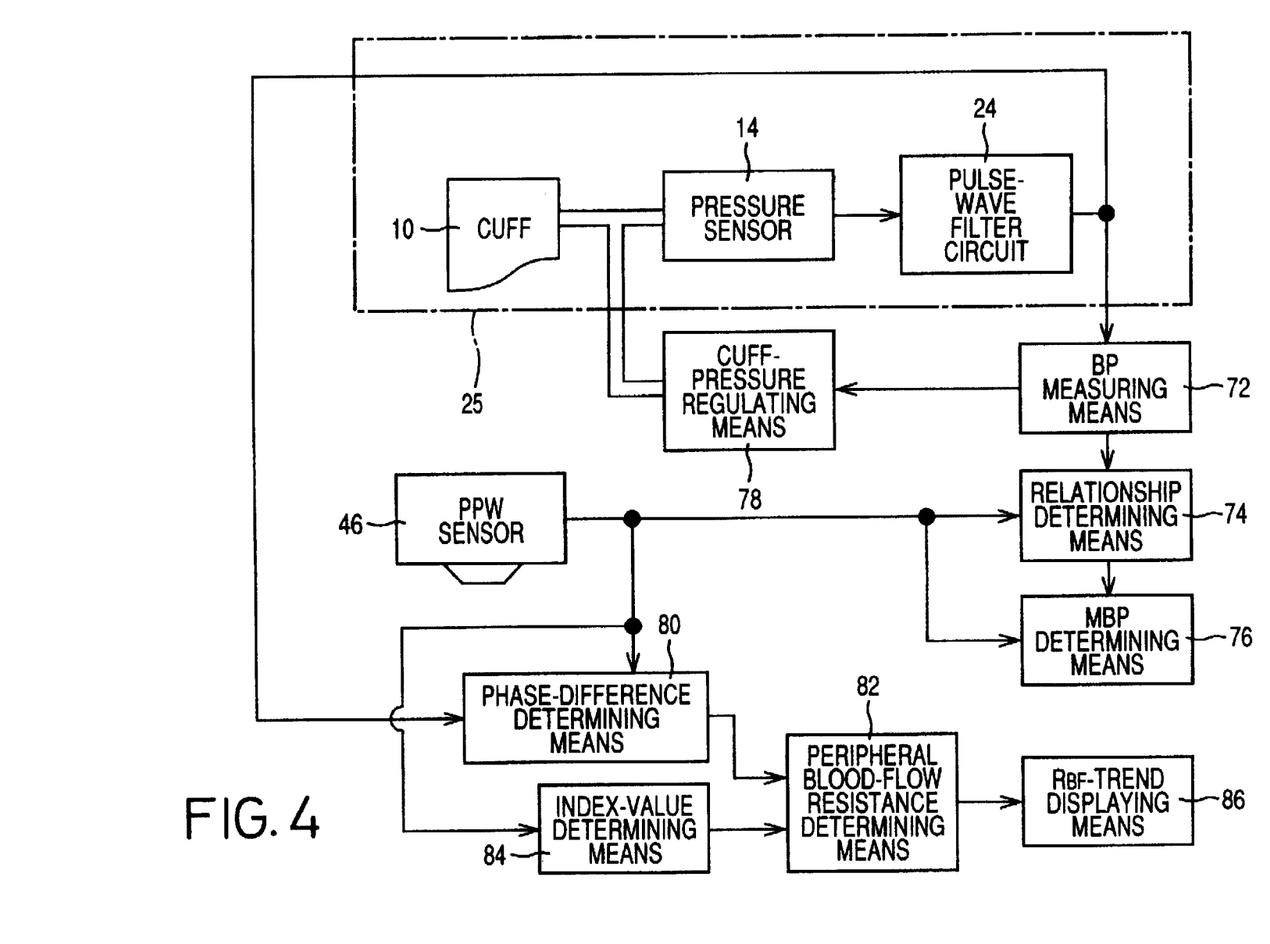
FIG. 4 is a diagrammatic view for explaining various functions of the control device of the BP monitor of FIG. 1.

The pulse-wave filter circuit 24 includes a band-pass filter which extracts, from the pressure signal SP, a pulse-wave signal, $SM_1$, representative of an oscillating or alternating-current component of the pressure signal SP, based on a frequency characteristic of the signal $SM_1$. The pulse-wave signal $SM_1$ is supplied via a second A/D converter 30 to the control device 28. The alternating-current component represented by the pulse-wave signal $SM_1$ corresponds to an oscillatory pressure wave, i.e., pulse wave which is produced from a brachial artery (not shown) of the patient in synchronism with the heartbeat of the patient and is propagated via skin tissue to the cuff 10. This pulse wave is referred to as the "cuff pulse wave" to be distinguished from a "pressure pulse wave" which will be described later. An example of the cuff pulse wave is shown in an upper portion of the graph of FIG. 2. In the present embodiment, the cuff 10, the pressure sensor 14, and the pulse-wave filter circuit 24 cooperate with one another to provide a first pulse wave sensor 25 (FIG. 4).

The control device 28 is provided by a microcomputer including a central processing unit (CPU) 29, a read only memory (ROM) 31, a random access memory (RAM) 33, and an input and output (I/O) port (not shown). The CPU 29 processes input signals, including the signals SK, $SM_1$, by utilizing the temporary-storage function of the RAM 33, according to control programs pre-stored in the ROM 31. In addition, the CPU 29 supplies drive signals via the I/O port to drive circuits (not shown) associated with the selector valve 16 and the air pump 18, respectively. Thus, the CPU 29 controls respective operations of the valve 16 and the pump 18. For example, when an oscillometric BP measurement using the cuff 10 is carried out to calibrate the present BP monitor 8, the CPU 29 controls the valve 16 and the pump 18 to increase quickly the cuff pressure up to a predetermined target value and subsequently decrease the cuff pressure at a low rate of 2 to 3 mmHg/sec. Based on the variation of the cuff pulse wave represented by the pulse-wave signal $SM_1$ provided by the pulse-wave filter circuit 24 during the low-rate decreasing of the cuff pressure, the CPU 29 determines a systolic and a diastolic BP value of the patient, according to a known oscillometric BP measuring method. In addition, the CPU 29 controls a display 32 to display the thus determined BP values.

A pressure-pulse-wave (PPW) detecting probe 34 includes a container-like sensor housing 36, and a fastening band 40 connected to the sensor housing 36. With the help of the fastening band 40, the PPW detecting probe 34 is detachably attached to a wrist 42 of the same arm 12 of the patient on which the cuff 10 is worn, or the other arm of the patient, such that an opening of the sensor housing 36 is opposed to a body surface 38 of the patient. A PPW sensor 46 is secured via an elastic diaphragm 44 to inner surfaces of the sensor housing 36 such that the PPW sensor 46 is movable relative to the housing 36 and is advanceable through the opening of the housing 36 toward the body surface 38 of the patient. The sensor housing 36 and the diaphragm 44 cooperate with each other to define a pressure chamber 48, which is supplied with pressurized air from a second air pump 50 via a pressure regulator valve 52. Thus, the PPW sensor 46 is pressed on the body surface 38 with a pressing force, $P_{HD}$, corresponding to the air pressure of the pressure chamber 48. In the present embodiment, the pressing forces of the PPW sensor 46 applied to the body surface 38 or the radial artery 56 are indicated in terms of the pressure values (mmHg) of the pressure chamber 48. The sensor housing 36, the diaphragm 44, the pressure chamber 48, the second air pump 50, the pressure regulator valve 52, etc. cooperate with one another to provide a pressing device which presses the PPW sensor 46 against the radial artery 56 via the body surface or skin tissue 38.

The PPW sensor 46 includes a semiconductor chip formed of a monocrystalline silicon which has a press surface 54, and a number of pressure-sensing semiconductor elements (not shown) which are arranged, in the press surface 54, in an array at a regular interval of distance (about 0.2 mm), such that the array of pressure-sensing elements extends in the direction of width of the radial artery 56. When the PPW sensor 46 is pressed against the radial artery 56 via the body surface 38 of the wrist 42, the PPW sensor 46 detects an oscillatory pressure wave, i.e., pressure pulse wave (PPW) which is produced from the radial artery 56 in synchronism with the heartbeat of the patient and is propagated via the body surface 38 to the PPW sensor 46. The PPW sensor 46 generates a PPW signal, $SM_2$, representing the detected PPW, and supplies the PPW signal $SM_2$ to the control device 28 via a third A/D converter 58. An example of the pressure pulse wave (PPW) detected by the PPW sensor 46 is shown in a lower portion of the graph of FIG. 2, along the same time axis as that of the cuff pulse wave detected by the first pulse wave sensor 25 and shown in the upper portion of the graph. The PPW sensor 46 provides a second pulse wave sensor.

The CPU 29 of the control device 28 processes the input signals, including the PPW signal $SM_2$, by utilizing the temporary-storage function of the RAM 33, according to the control programs pre-stored in the ROM 31, and supplies drive signals to drive circuits (not shown) associated with the second air pump 50 and the pressure regulator valve 52, respectively. Thus, the CPU 29 controls respective operations of the pump 50 and the valve 52 to regulate the pressure of the pressure chamber 48 applied to the PPW sensor 46, i.e., the pressing force of the PPW sensor 46 applied to the radial artery 56 via the body surface or skin tissue 38.

When a continuous BP monitoring operation is carried out, the CPU 29 determines an optimum pressing force, $P_{HDP}$, of the PPW sensor 46 applied to the radial artery 56, based on the PPW detected by the PPW sensor 46 while the pressure of the pressure chamber 48 is slowly changed, and controls the pressure regulator valve 52 to maintain the pressure of the chamber 48 at the determined optimum pressing force $P_{HDP}$. In addition, the CPU 29 determines a relationship between BP values and PPW magnitudes $P_M$ (i.e., voltage values of the PPW signal $SM_2$), based on a systolic and a diastolic BP value, SAP, DAP, measured using the cuff 10 according the oscillometric BP measuring method, and a maximum and a minimum magnitude, $P_{Mmax}$, $P_{Mmin}$, of one heartbeat-synchronous pulse of the PPW detected by the PPW sensor 46 being pressed on the body surface 38 with the optimum pressing force $P_{HDP}$. According to the thus determined relationship, the CPU 29 determines a systolic and a diastolic BP value (i.e., monitor BP values), $MBP_{SYS}$, $MBP_{DIA}$, of the patient, based on a maximum magnitude (i.e., upper-peak magnitude) $P_{Mmax}$ and a minimum magnitude (i.e., lower-peak magnitude), $P_{Mmin}$, of each of successive heartbeat-synchronous pulses of the PPW detected by the PPW sensor 46 being pressed with the optimum pressing force $P_{HDP}$. Subsequently, the CPU 29 controls the display 32 to successively display, for each heartbeat-synchronous pulse, the thus determined monitor BP values $MBP_{SYS}$, $MBP_{DIA}$, in digits, and continuously display the waveform of the PPW detected by the PPW sensor 46. This waveform represents the instantaneous monitor BP values MBP of the patient.

Figure 3:
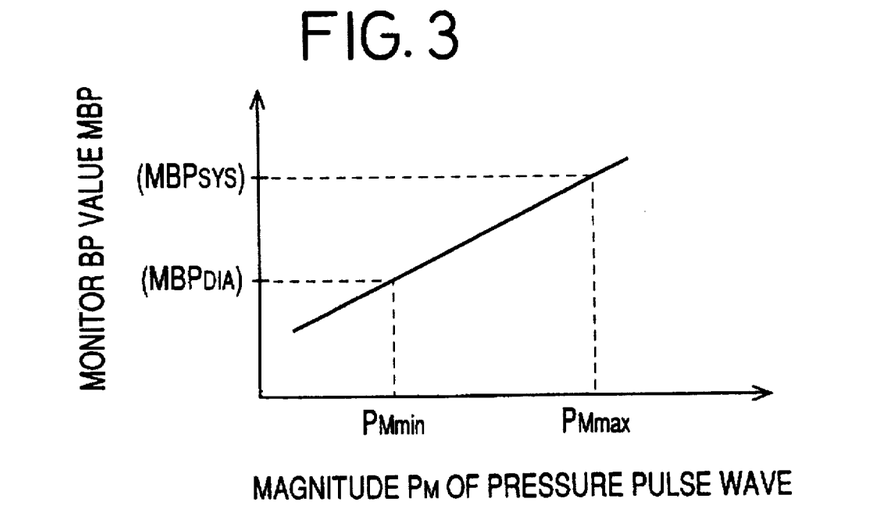
FIG. 3 is a graph showing a relationship determined by a control device of the BP monitor of FIG. 1.

FIG. 3 shows an example of a relationship between BP values (monitor BP values MBP) and PPW magnitudes, $P_M$, that is determined by the CPU 29. This relationship is expressed by the following linear function (1):

$$MBP = A \cdot P_M + B \qquad (1)$$

where A is a constant corresponding to the slope of the linear function (1) and B is a constant corresponding to the intercept of the axis of ordinate indicative of the monitor BP values MBP.

FIG. 4 illustrates various functions of the electronic control device 28 of the present BP monitor 8. The static-pressure filter circuit 22 cooperates with the control device 28 to provide a BP measuring device 72 which measures, according to the oscillometric BP measuring method (JIS T 1115; JIS is Japanese Industrial Standard), a systolic BP value SAP and a diastolic BP value DAP of a living subject based on the variation of respective amplitudes of heartbeat-synchronous pulses of the cuff pulse wave detected by the first pulse wave sensor 25 while the pressure of the cuff 10 is slowly increased or decreased at the rate of 2 to 3 mmHg/sec. The cuff pulse wave is represented by the pulse-wave signal $SM_1$ provided by the pulse-wave filter circuit 24. The PPW sensor 46 is preferably worn on the wrist of the other arm of the patient different from the arm 12 on which the cuff 10 is worn, and detects the PPW produced from the radial artery of the other arm. The PPW sensor 46 provides a second pulse wave sensor. The control device 28 functions as relationship determining means 74 for determining a MBP-$P_M$ relationship between monitor BP values MBP and PPW magnitudes $P_M$ that is expressed by the linear function (1) and is shown in FIG. 3, based on the PPW detected by the PPW sensor 46 and the BP values measured by the BP measuring device 72. The control device 28 also functions as monitor-BP-value (MBP) determining means 76 for successively determining, according to the MBP-$P_M$ relationship, a monitor BP value MBP of the subject based on a magnitude of each of heartbeat-synchronous pulses of the PPW detected by the PPW sensor 46. The selector valve 16 and the first air pump 18 cooperate with the control device 28 to provide a cuff-pressure regulating device 78 which regulates the air pressure of the cuff 10 (i.e., cuff pressure), that is detected by the pressure sensor 14 when each oscillometric BP measurement using the cuff 10 is carried out. The cuff-pressure regulating device 78 changes the cuff pressure according to a well-known procedure, so that the BP measuring device 72 can measure BP values of the patient using the cuff 10 at a regular interval of time and the relationship determining means 74 calibrates or updates the MBP-$P_M$ relationship based on the BP values measured using the cuff 10. For example, the regulating device 78 increases the cuff pressure up to a target value, e.g., 180 mmHg, which is higher than an estimated systolic BP value of the patient and subsequently decreases the cuff pressure slowly at the rate of 2 to 3 mmHg/sec, during a measurement period in which BP values of the patient are determined by the BP measuring device 72 according to a well-known oscillometric BP determining algorithm. After the BP measuring operation, the regulating device 78 quickly deflates the cuff 10. In addition, during a continuous BP monitoring operation, the regulating device 78 maintains the cuff pressure at a predetermined hold pressure sufficiently lower than a diastolic BP value DAP of the patient, so that the first pulse wave sensor 25 detects the cuff pulse wave (i.e., first pulse wave) from the cuff 10 being held at the predetermined hold pressure.

Figure 2:
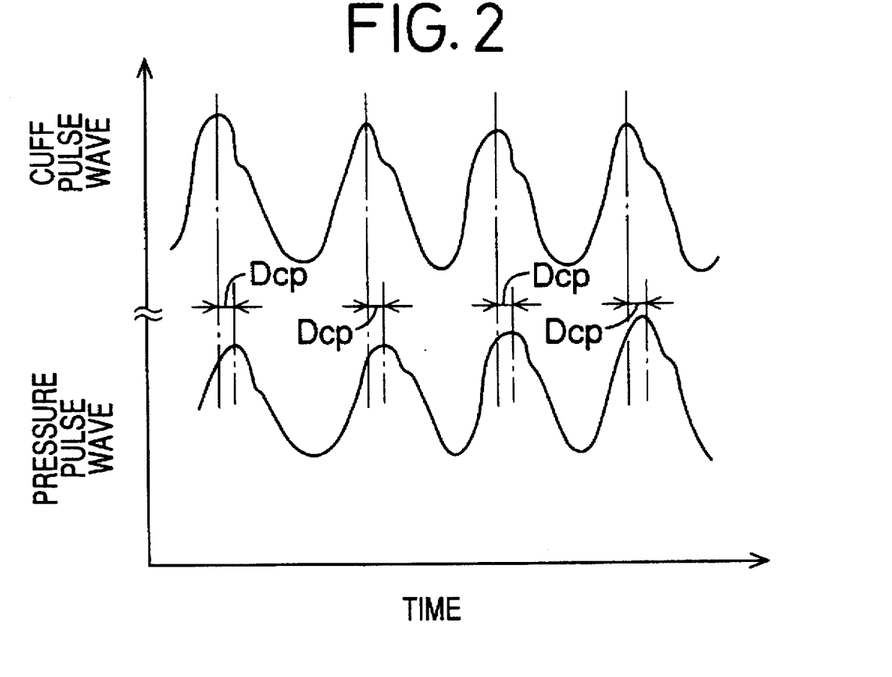
FIG. 2 is a graph showing an example of a cuff pulse wave provided by a pulse-wave filter circuit of the BP monitor of FIG. 1, and an example of a pressure pulse wave (PPW) detected PPW sensor of the BP monitor of FIG. 1.

Moreover, the control device 28 functions as phase-difference determining means 80. During a continuous BP monitoring operation in which monitor BP values MBP of the patient are successively determined by the MBP determining means 76, the phase-difference determining means 80 successively determines a phase difference, $D_{CP}$ (msec), of each of heartbeat-synchronous pulses of the cuff pulse wave (first pulse wave) obtained from the cuff 10 being held at the above-described hold pressure and a corresponding one of heartbeat-synchronous pulses of the pressure pulse wave (second pulse wave) detected by the PPW sensor 46 from the radial artery 56. The phase differences $D_{CP}$ determined by the phase-difference determining means 80 are shown in the graph of FIG. 2. The first and second pulse wave sensors 25, 46 are worn on the different arms of the patient, respectively, or the two different portions of the same arm 12 of the patient, respectively.

The control device 28 also functions as peripheral blood-flow resistance determining means 82 for successively determining a peripheral blood-flow resistance, $R_{BF}$, of the patient, based on each phase difference determined by the phase-difference determining means 80, according to a predetermined relationship between peripheral blood-flow resistance $R_{BF}$ and phase difference $D_{CP}$. The peripheral blood-flow resistance $R_{BF}$ determined by the peripheral blood-flow resistance determining means 82 is defined as an index, MBF/MAP, where MAP is a mean BP value (mmHg) of the patient and MBF is a mean blood flow rate (cm$^3$/sec) at a peripheral portion or tissue of the patient.

Figure 5:
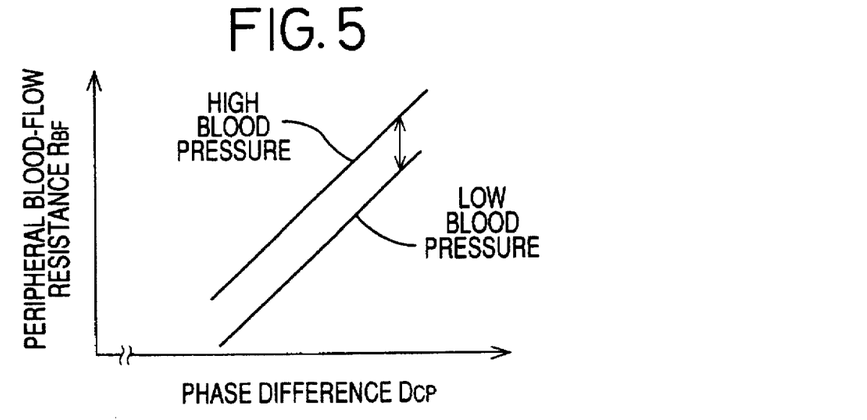
FIG. 5 is a graph showing a predetermined relationship between phase difference or blood pressure and peripheral blood-flow resistance, pre-stored in the control device of the BP monitor of FIG. 1.
Figure 6:
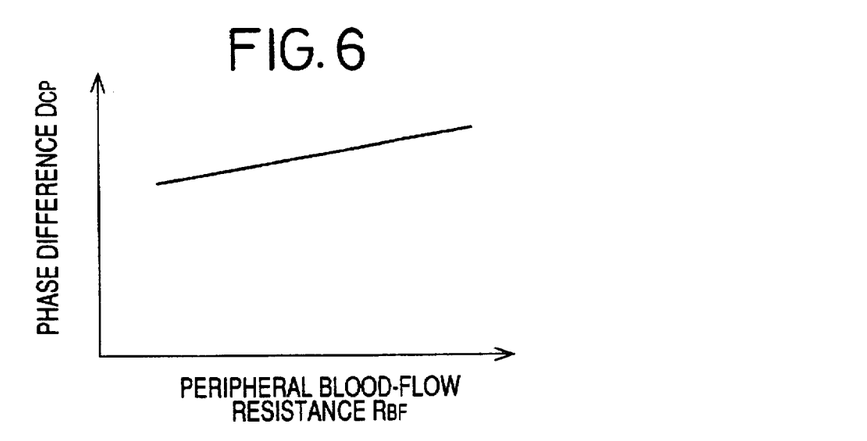
FIG. 6 is a graph showing a basic relationship between peripheral blood-flow resistance and phase difference.
Figure 7:
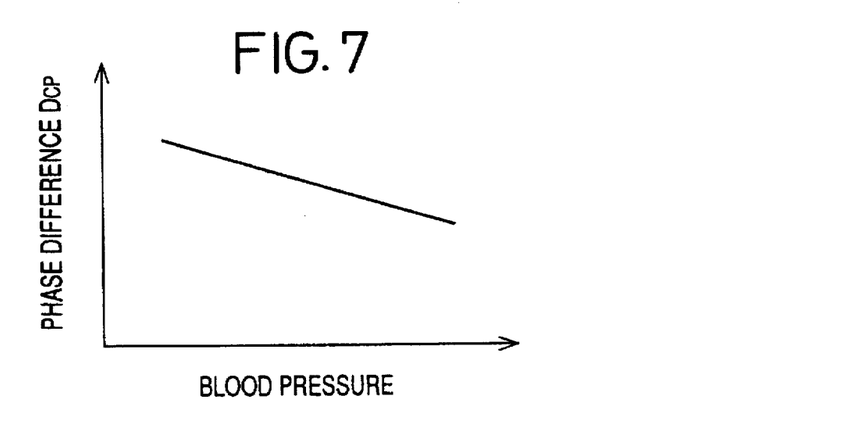
FIG. 7 is a graph showing a relationship between blood pressure and phase difference.

In the present embodiment, the peripheral blood-flow resistance determining means 82 determines the peripheral blood-flow resistance $R_{BF}$ based on a phase difference and a BP value of the patient, according to a function of phase difference $D_{CP}$ and blood pressure BP as variables shown in the graph of FIG. 5. FIG. 6 shows a basic relationship between peripheral blood-flow resistance $R_{BF}$ and phase difference $D_{CP}$, and FIG. 7 shows a relationship between blood pressure and phase difference $D_{CP}$. The relationship shown in FIG. 5 is derived from the two relationships shown in FIGS. 6 and 7.

Figure 8:
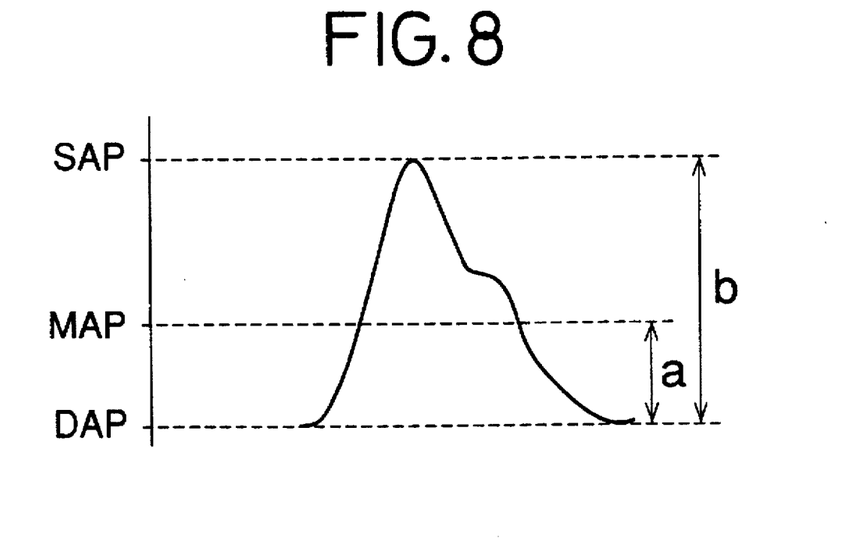
FIG. 8 is a graph for explaining the definition of an index, %MAP, indicative of a characteristic of the waveform of a decreasing portion of each heartbeat-synchronous pulse of PPW detected by the PPW sensor of the BP monitor of FIG. 1.
Figure 9:
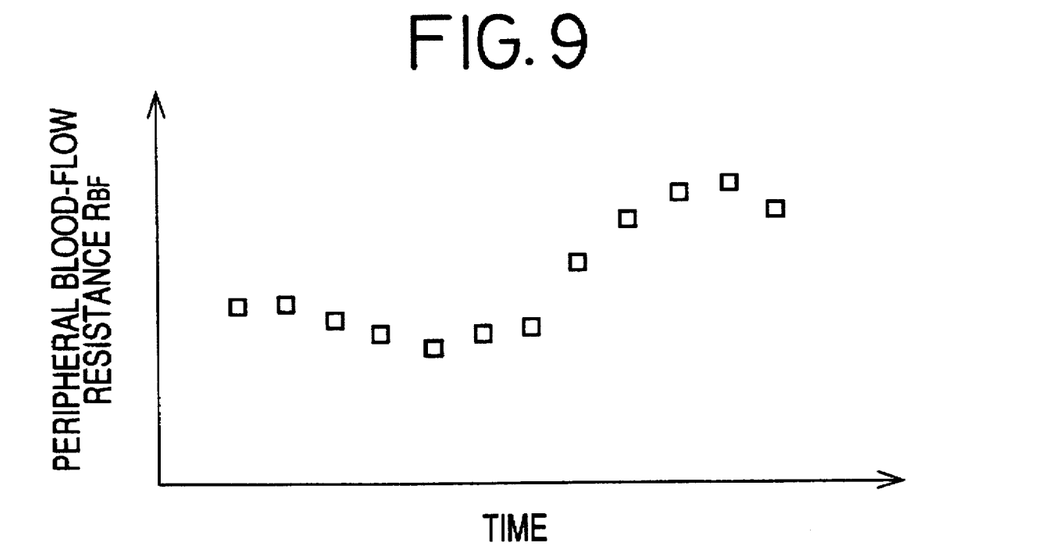
FIG. 9 is a graph showing a time-wise trend of peripheral blood-flow resistance values determined by the BP monitor of FIG. 1.

The control device 28 further functions as index-value determining means 84 for determining an index value indicative of a characteristic of the waveform of a decreasing portion of each of heartbeat-synchronous pulses of the PPW detected by the PPW sensor 46, so that the peripheral blood-flow resistance determining means 82 corrects, based on the index value determined by the index-value determining means 84, the peripheral blood-flow resistance $R_{BF}$ determined based on the phase difference determined by the phase-difference determining means 80. For example, the index value determined by the index-value determining means 84 may be a curvature of the waveform of a specific range of the decreasing portion of each pulse of the PPW, a time constant of the decreasing portion, or a value, %MAP. The waveform of the decreasing (or diastolic-period) portion of each PPW pulse reflects a flexibility or softness of the radial artery 56. In particular, the index %MAP is defined as a/b×100% as indicated in the graph of FIG. 8, where b is an amplitude obtained by subtracting a minimum magnitude corresponding to a diastolic BP value DAP from a maximum magnitude corresponding to a systolic BP value SAP and a is a height of a magnitude corresponding to a mean BP value MAP, obtained by subtracting the minimum magnitude from a magnitude corresponding to the mean BP value MAP. The systolic, diastolic, and mean BP values SAP, DAP, MAP are measured by the BP measuring device 72. Otherwise, the value a may be defined as a height of the center of gravity of an area defined by the waveform of each pulse of the PPW and the base line corresponding to the diastolic BP value DAP. Since peripheral blood-flow resistance may be defined by a function of index %MAP as a variable, the peripheral blood-flow resistance determining means 82 may determine, according to that function, another or second peripheral blood-flow resistance of the subject based on an index value %MAP determined with respect to each pulse of the PPW, and may correct, based on each second peripheral blood-flow resistance, a corresponding first peripheral blood-flow resistance $R_{BF}$ determined based on a corresponding phase difference $D_{CP}$. For example, each pair of first and second peripheral blood-flow resistance values are multiplied by a first weighed coefficient, $\alpha$ ($0<\alpha<1$), and a second weighed coefficient, $\beta$ ($0<\beta<1$, $\alpha+\beta=1$), respectively, to obtain two products the sum of which provides a corrected peripheral blood-flow resistance $R_{BF}$. The control device 28 functions as $R_{BF}$-trend displaying means 86 for controlling the display 32 to display, along a time axis in a screen image thereof, a time-wise trend of respective values of peripheral blood-flow resistance $R_{BF}$ successively determined and corrected by the peripheral blood-flow resistance determining means 82. FIG. 9 shows an example of time-wise trend of the peripheral blood-flow resistance values $R_{BF}$.

Next, there will be described the operation of the BP monitor 8 constructed as described above, by reference to the flow charts of FIGS. 10 and 11 representing the control programs pre-stored in the ROM 31.

Figure 10:
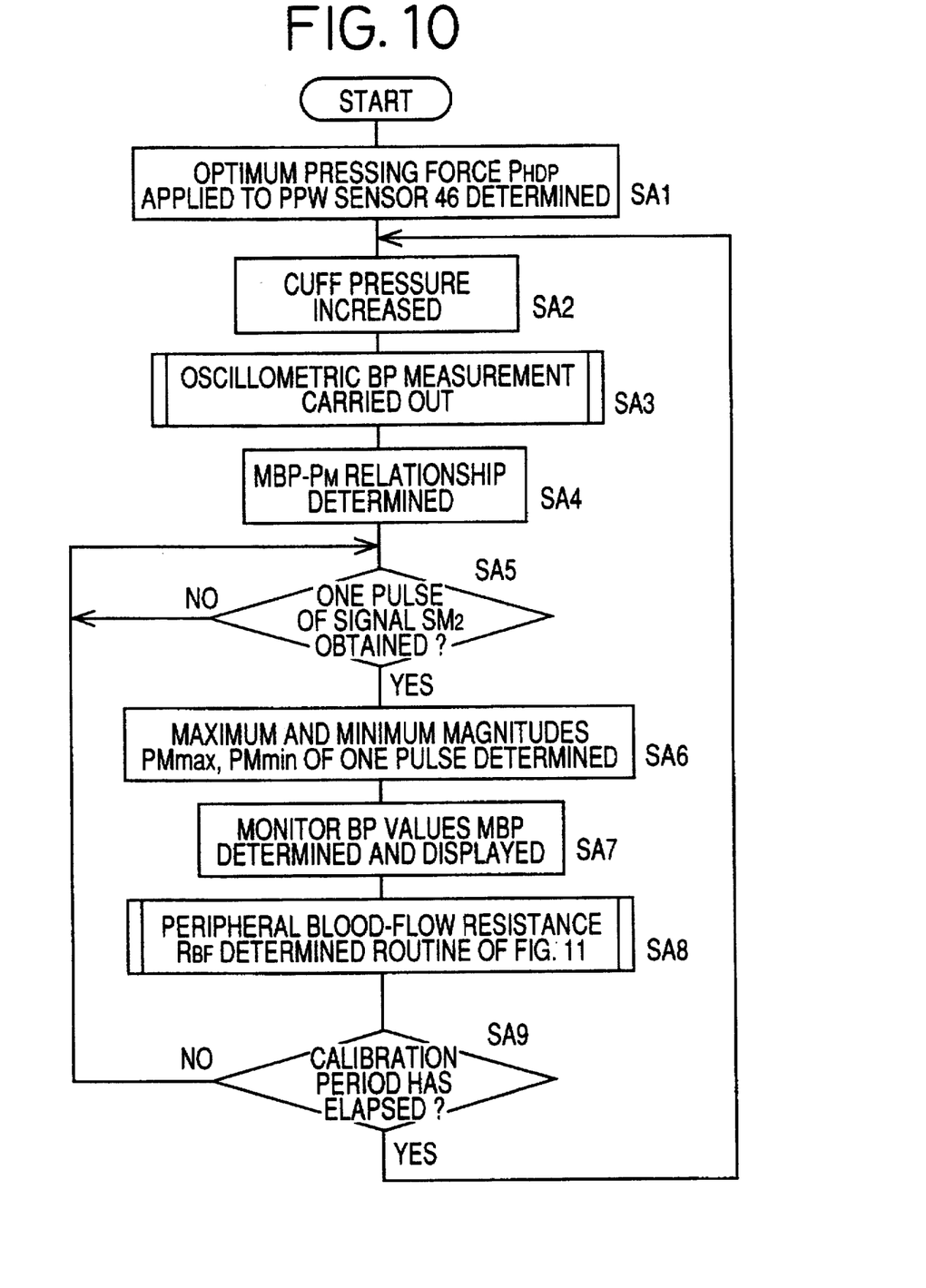
FIG. 10 is a flow chart representing a main control routine according to which the BP monitor of FIG. 1 operates.

First, at Step SA1, the CPU 29 of the control device 28 controls the second air pump 50 and the pressure regulator valve 52 to increase slowly the pressure of the pressure chamber 48, and determines, as an optimum pressing force $P_{HDP}$, a pressure $P_{HD}$ of the chamber 48 when the PPW sensor 46 detects a maximum pulse having the greatest amplitude of respective amplitudes of all the pulses detected thereby during the slow increasing of the pressure of the chamber 48. Subsequently, the CPU 29 maintains or holds the pressure of the chamber 48 at the thus determined optimum pressing force $P_{HDP}$. Thus, the optimum pressing force $P_{HDP}$ is applied to the PPW sensor 46 to press the radial artery 56 via the body surface 38.

Next, the control of the CPU 29 proceeds with Step SA2 to start increasing the pressure of the cuff 10 for measuring actual BP values of the patient. Step SA2 corresponds to the cuff-pressure regulating device 78. Step SA2 is followed by Step SA3 to carry out a known oscillometric BP determining algorithm. Specifically described, the selector valve 16 is switched to the first state and the first air pump 18 is operated, so the cuff pressure continues to increase up to a target pressure (e.g., 180 mmHg) higher than an estimated systolic BP value of the patient. Subsequently, the air pump 18 is stopped and the selector valve 16 is switched to the second state, so that the cuff pressure decreases at a predetermined low rate (e.g., about 3 mmHg/sec). Based on the variation of respective amplitudes of heartbeat-synchronous pulses of the cuff-pulse-wave (CPW) signal $SM_1$ obtained during this slow decreasing of the cuff pressure, the CPU 29 determines a systolic, a mean, and a diastolic BP value SAP, MAP, DAP of the patient according to the oscillometric BP determining algorithm. More specifically, the CPU 29 determines, as the systolic BP value SAP, a cuff pressure at the time when the pulse amplitudes significantly largely increase, determines, as the diastolic BP value DAP, a cuff pressure at the time when the pulse amplitudes significantly largely decrease, and determines, as the mean BP value MAP, a cuff pressure at the time when the pulse amplitudes become maximum. In addition, the CPU 29 determines a pulse rate of the patient based on the interval of time between respective upper peaks of two successive heartbeat-synchronous pulses of the CPW signal $SM_1$. The thus measured BP values and pulse rate are stored in the RAM 33 and displayed by the display device 32. Then, the selector valve 16 is switched to the third state and then to the first state, so that the cuff pressure is first quickly decreased and then is held at a hold pressure which is pre-determined to be sufficiently lower than the measured diastolic BP value DAP. Step SA3 corresponds to the BP measuring means 72.

Subsequently, the control of the CPU 29 goes to Step SA4 to determine a relationship between monitor BP value MBP and magnitude $P_M$ of pressure pulse wave (i.e., voltage of the pressure-pulse-wave (PPW) signal $SM_2$) as shown in FIG. 3. More specifically, the CPU 29 newly reads in one heartbeat-synchronous pulse of the PPW signal $SM_2$ supplied from the PPW sensor 46, determines a maximum and a minimum magnitude $P_{Max}$, $P_{Min}$, of the one pulse, and determines the previously-indicated linear function (1) based on the systolic and diastolic BP values SAP, DAP of the patient measured at Step SA3 and the thus determined maximum and minimum magnitudes $P_{Mmax}$, $P_{Mmin}$, of the one pulse of the PPW signal $SM_2$. Step SA4 corresponds to the relationship determining means 74.

After the MBP-$P_M$ relationship shown in FIG. 3 is determined at Step SA4, the control of the CPU 29 goes to Step S5 to judge whether the CPU 29 has read in one heartbeat-synchronous pulse of the PPW signal $SM_2$ supplied from the PPW sensor 46 being pressed at the optimum pressing force $P_{HDP}$ and has read in a corresponding heartbeat-synchronous pulse of the CPW signal $SM_1$ obtained from the cuff 10 being held at the low hold pressure. If a negative judgment is made at Step SA5, the CPU 29 waits for detecting one pulse of each of the PPW and CPW signals $SM_1$, $SM_2$. Meanwhile, if a positive judgment is made at Step SA5, the control of the CPU 29 goes to Step SA6 to determine a maximum (upper-peak) magnitude $P_{Max}$ and a minimum (lower-peak) magnitude $P_{Mmin}$, of the one pulse of the PPW signal $SM_2$. Step SA6 is followed by Step SA7 to determine a systolic and a diastolic BP value $MBP_{SYS}$, $MBP_{DIA}$ (monitor BP values) of the patient, based on the maximum and minimum magnitudes $P_{Mmax}$, $P_{Mmin}$, of the one pulse of the PPW signal $SM_2$ determined at Step SA6, according to the MBP-$P_M$ relationship determined at Step SA4. The CPU 29 controls the display device 32 to display, on its image screen, not only the thus determined monitor BP values MBP but also the waveform of the one pulse that is continuous with the waveforms of the previous pulses. Steps SA6 and SA7 correspond to the MBP determining means 76.

Figure 11:
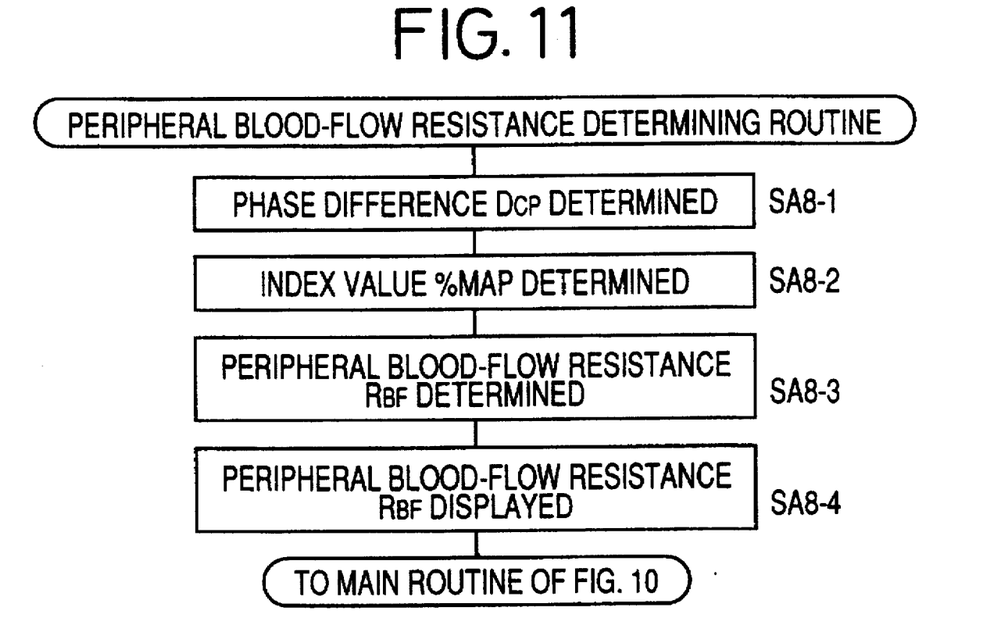
FIG. 11 is a flow chart representing a peripheral blood-flow resistance determining routine as one step of the main routine of FIG. 10.

Subsequently, the control of the CPU 29 goes to Step SA8, i.e., peripheral blood-flow resistance determining routine represented by the flow chart of FIG. 11. At Step SA8-1, the CPU 29 determines a phase difference $D_{CP}$ (msec) of the one pulse of the CPW signal $SM_1$ and the corresponding pulse of the PPW signal $SM_2$, based on the signals SM1, SM2 read in at Step SA5. For example, the CPU 29 determines, as the phase difference $D_{CP}$, a time interval between the respective Upper peaks of the one pulse of the CPW signal $SM_1$ and the corresponding pulse of the PPW signal $SM_2$, as shown in FIG. 2. Step SA8-1 corresponds to the phase-difference determining means 80.

Step SA8-1 is followed by Step SA8-2 to determine an index value %MAP indicative of a characteristic of the waveform of a decreasing portion of the one pulse of the PPW signal $SM_2$ read in at Step SA5. The CPU 29 determines, as the index value %MAP, a ratio a/b ($\times 100\%$) of a height or magnitude a of the center of gravity of the area of the one pulse to a pulse amplitude b of the one pulse, as shown in FIG. 8. The height or magnitude a of the center of gravity of the area of the one pulse substantially corresponds to the mean BP value MAP of the subject measured at Step SA3. Step SA8-2 corresponds to the index-value determining means 84. Step SA8-2 is followed by Step SA8-3 to determine a peripheral blood-flow resistance $R_{BF}$ of the patient based on the actual phase difference $D_{CP}$ determined at Step SA8-1 and the BP value of the patient (the monitor or estimated BP value MBP determined at Step SA7, or the actual BP value AP measured at Step SA3), according to the relationship, shown in FIG. 5, which is pre-determined and is pre-stored in the ROM 31. In the case where the relationship is pre-determined based on systolic blood pressure values of human beings, the CPU 29 determines the resistance $R_{BF}$ based on the monitor systolic BP value $MBP_{SYS}$ or the actual systolic BP value SAP; and, in the case where the relationship is pre-determined based on diastolic blood pressure values of human beings, the CPU 29 determines the resistance $R_{BF}$ based on the monitor diastolic BP value $MBP_{DIA}$ or the actual diastolic BP value DAP.

At Step SA8-3, the CPU 29 corrects, based on the index value %MAP determined at Step SA8-2, the resistance $R_{BF}$ determined according to the relationship shown in FIG. 5. The resistance $R_{BF}$ that relates to the flexibility or softness of the walls of arteries of the patient is also a function of index value %MAP and BP value of the patient. Accordingly, the CPU 29 determines a second peripheral blood-flow resistance $R_{BF2}$ based on the index value %MAP solely, or the index value %MAP and BP value in combination. The CPU 29 determines a weighed average of the first and second resistances $R_{BF}$, $R_{BF2}$ by multiplying the two resistances $R_{BF}$, $R_{BF2}$ by a first and a second weighing coefficient $\alpha$, $\beta$ ($0<\alpha$, $\beta<1$; $\alpha+\beta=1$), respectively, and summing the thus obtained two products. Step SA8-3 corresponds to the peripheral blood-flow resistance determining means 82. However, this correction may be omitted.

Step SA8-3 is followed by Step SA8-4 to control the display device 32 to display, on the screen thereof, a time-wise trend of the corrected peripheral blood-flow resistance values $R_{BF}$ along an axis indicative of time as shown in FIG. 9. Step SA8-4 corresponds to the $R_{BF}$-trend displaying means.

Step SA8 is followed by Step SA9 to judge whether a predetermined period (i.e., calibration period) of about 10 to 20 minutes has elapsed after a BP measurement using the cuff 10 is carried out at Step SA3 in the current control cycle. If a negative judgment is made at Step SA9, the CPU 29 repeats Step SA5 and the following steps including Step SA8, so that a monitor systolic BP value $MBP_{SYS}$ and a monitor diastolic BP value $MBP_{DIA}$ of the patient are determined for each heartbeat-synchronous pulse of the PPW signal $SM_2$ and displayed by the display device 32. Meanwhile, if a positive judgment is made at Step SA9, the control of the CPU 29 goes back to Step SA2 and the following steps to update the $MBP$-$P_M$ relationship shown in FIG. 3.

As is apparent from the foregoing description, in the present BP monitor 8, the phase difference $D_{CP}$ is determined based on the cuff pulse wave (first pulse wave) detected by the first pulse wave sensor 25 and the pressure pulse wave (second pulse wave) detected by the PPW sensor (second pulse wave sensor) 46, at Step SA8-1, and the peripheral blood-flow resistance $R_{BF}$ of the patient is determined based on the phase difference $R_{BF}$ according to the relationship shown in FIG. 5, at Step SA8-3. The first and second pulse wave sensors 25, 46 are worn on different portions of the patient. A higher resistance $R_{BF}$ indicates a worse peripheral blood-flow condition or state of the patient; and a lower resistance $R_{BF}$ indicates a better peripheral blood-flow condition of the patient. Thus, the resistance $R_{BF}$ well reflects the peripheral blood-flow condition of the patient. Thus, the present BP monitor can monitor, with high accuracy, the peripheral blood-flow condition of the patient.

When the present BP monitor 8 determines a peripheral blood-flow resistance $R_{BF}$ of the patient at Step SA8-3, the CPU 29 utilizes the function of phase difference $D_{CP}$ and BP value as variables, shown in FIG. 5. That is, the CPU 29 determines, according to this function, a resistance $R_{BF}$ of the patient based on an actual BP value AP measured at Step SA3 or a monitor BP value MBP determined at Step SA7, in addition to the phase difference $D_{CP}$ determined at Step SA8-1. Thus, the BP monitor 8 can determine, with higher accuracy, the peripheral blood-flow resistance values $R_{BF}$ of the subject. Resistance $R_{BF}$ is a function of not only phase difference $D_{CP}$ but also BP value.

In addition, at Step SA8-2, the CPU 29 determines an index value %MAP indicative of a characteristic of the waveform of a decreasing portion of each heartbeat-synchronous pulse of the PPW signal $SM_2$. At Step SA8-3, the CPU 29 corrects, based on the index value %MAP, the peripheral blood-flow resistance value $R_{BF}$ determined based on the phase difference $D_{CP}$ and the BP value of the subject according to the relationship shown in FIG. 5. Thus, the BP monitor 8 can determine, with still higher accuracy, the peripheral blood-flow resistance values $R_{BF}$ of the subject.

Moreover, at Step SA8-4, the present BP monitor 8 controls the display device 32 to display a time-wise trend of the peripheral blood-flow resistance values $R_{BF}$ of the subject which have been determined for the respective heartbeat-synchronous pulses of the CPW or PPW signal $SM_1$ or $SM_2$ obtained at Step SA5. Thus, a medical person such as a doctor or nurse can easily read the time-wise change of the resistance $R_{BF}$ of the patient by just observing the screen image of the display device 32.

The BP monitor 8 measures actual BP values AP of the patient by using the cuff 10 being worn on the patient, the pressure sensor 14 for detecting the cuff pressure, and the pulse-wave filter circuit 24 for extracting; from the cuff pressure detected by the sensor 14, the cuff pulse wave that is an oscillatory pressure wave produced in the cuff 10 in synchronism with the heartbeat of the patient. The cuff 10, the sensor 14, and the filter circuit 24 also function as the first pulse wave sensor 25 for detecting the cuff pulse wave as the first one of the two sorts of pulse waves whose phase difference is utilized to determine the peripheral blood-flow resistance $R_{BF}$ of the patient. Thus, no exclusive first pulse wave sensor is needed for detecting the first pulse wave and accordingly the BP monitor 8 enjoys a simple construction.

Similarly, the PPW sensor 46 that is pressed against the artery 56 of the patient via the body surface 38 to detect the pressure pulse wave produced from the artery 56, also functions as the second pulse wave sensor for detecting the second pulse wave. Thus, no exclusive second pulse wave sensor is needed for detecting the second pulse wave and eventually determining the peripheral blood-flow resistance $R_{BF}$ of the patient, and accordingly the BP monitor 8 enjoys a simpler construction.

While the present invention has been described in its preferred embodiments, the present invention may otherwise be embodied.

For example, although in the illustrated embodiment the CPU 29 determines the peripheral blood-flow resistance $R_{BF}$ based on the phase difference $D_{CP}$ and the actual or monitor BP value AP or MBP according to the relationship (i.e., function of two variables $D_{CP}$, AP (or MBP) shown in FIG. 5, it is possible to determine a peripheral blood-flow resistance of a patient based on a phase difference $D_{CP}$ according to the relationship (i.e., function of phase difference $D_{CP}$) shown in FIG. 6. In addition, the CPU 29 may determine a peripheral blood-flow resistance based on an actual index value %MAP according to a function of index value %MAP and BP value AP (or MBP) or a function of index value %MAP. In the last case, the first pulse wave sensor 25 may be omitted.

In the illustrated embodiment, the first pulse wave sensor 25 is provided by the cuff 10, the pressure sensor 14, and the pulse-wave filter circuit 24 all of which are employed for measuring actual BP values of a patient, and the second pulse wave sensor is provided by the PPW sensor 46 which is employed for detecting the pressure pulse wave and continuously monitoring the blood pressure of the patient. One or each of the first and second pulse wave sensors employed for determining the phase difference $D_{CP}$ of the first and second pulse waves may be provided by an exclusive pulse wave sensor which is independent of the function of measuring the BP values of the patient or the function of detecting the pressure pulse wave of the patient. The exclusive sensor may be, for example, an impedance-pulse-wave sensor which includes electrodes adapted to be held in contact with the surface of a body portion of a patient and detects an impedance pulse wave as the change of impedance of the body portion; a supersonic-pulse-wave sensor which is held in contact with the surface of a body portion of a patient, emits supersonic wave toward an artery of the body portion via the surface, and detects, as a supersonic pulse wave, the displacement or vibration of the wall of the artery; or a photoelectric-pulse-wave sensor which is adapted to be worn on the surface of a body portion of a patient, emits light toward the body portion, and detects, as a photoelectric pulse wave, the light reflected from, or transmitted through, the body portion of the subject. The photoelectric-pulse-wave sensor may be one which is employed by a pulse oximeter or a pulse-rate meter.

While in the illustrated embodiment the. CPU 29 determines, as the phase difference $D_{CP}$, the difference of respective times of detection of respective upper peaks of each CPW pulse and each PPW possible to den in FIG. 2, it is possible to determine, as the phase difference $D_{CP}$, the difference of respective times of detection of respective lower peaks of the two sorts of pulse waves.

Although the BP monitor 8 measures actual BP values of a patient according to an oscillometric BP measuring method, it is possible to employ a microphone for detecting Korotkoff sounds produced from the arteries underlying the cuff 10 and measures actual BP values of a patient according to a Korotkoff-sound BP measuring method in which a systolic and/or a diastolic BP value of the patient are/is determined based on the appearing and/or disappearing of the Korotkoff sounds detected by the microphone while the cuff pressure is changed.

It is to be understood that the present invention may be embodied with other changes, improvements, and modifications that may occur to those skilled in the art without departing from the spirit and scope of the invention defined in the appended claims.

What is claimed is:

1. An apparatus for monitoring a peripheral blood-flow condition of a living subject by detecting a peripheral blood-flow resistance of the subject, comprising:

a first and a second pulse-wave sensor which are adapted to be worn on a first and a second portion of the subject, respectively, to detect a first and a second pulse wave, respectively, each of which is produced in synchronism with a heartbeat of the subject;

phase-difference determining means for determining a difference of respective phases of said first and second pulse waves detected by said first and second pulse-wave sensors;

peripheral blood-flow resistance determining means for determining said peripheral blood-flow resistance of the subject, based on the phase difference determined by said phase-difference determining means, according to a predetermined relationship between peripheral blood-flow resistance and phase difference; and a blood pressure measuring device which measures a blood pressure of the subject, and wherein said peripheral blood-flow resistance determining means determines said peripheral blood-flow resistance of the subject, based on the phase difference determined by said phase-difference determining means and the blood pressure measured by said blood pressure measuring device, according to said predetermined relationship defined by a function of phase difference and blood pressure as variables.

2. An apparatus according to claim 1, wherein said blood pressure measuring device comprises an inflatable cuff adapted to be wound around a body portion of the subject, and measuring means for measuring said blood pressure of the subject by changing a pressure of said cuff applied to the body portion of the subject, and wherein said first pulse-wave sensor comprises said cuff, a pressure sensor which detects said pressure of the cuff, and a pulse-wave filter circuit which extracts, as said first pulse wave, an oscillatory pressure wave including a plurality of pulses produced in said cuff in synchronism with the heartbeat of the subject, from the cuff pressure detected by said pressure sensor.

3. An apparatus according to claim 2, further comprising a cuff-pressure regulating device which changes said pressure of said cuff to a predetermined value lower than a diastolic blood pressure of the subject and holds the cuff pressure at the predetermined value, and wherein said pulse-wave filter circuit extracts, as said first pulse wave, a plurality of heartbeat-synchronous pulses produced in said cuff held at said predetermined value, from the cuff pressure detected by said pressure sensor.

4. An apparatus according to claim 2, wherein said second pulse-wave sensor comprises a pressure pulse wave sensor which is adapted to be pressed against an artery of the subject via a skin of the subject, said pressure pulse wave sensor detecting, as said second pulse wave, a pressure pulse wave including a plurality of pulses produced from the artery of the subject in synchronism with the heartbeat of the subject.

5. An apparatus according to claim 1, further comprising index-value determining means for determining an index value indicative of a characteristic of a waveform of a decreasing portion of a heartbeat-synchronous pulse of said second pulse wave detected by said second pulse-wave sensor, wherein said peripheral blood-flow resistance determining means comprises correcting means for correcting, based on said index value determined by said index-value determining means, said peripheral blood-flow resistance determined based on said phase difference determined by said phase-difference determining means.

6. An apparatus according to claim 5, wherein said second pulse-wave sensor comprises a pressure pulse wave sensor which is adapted to be pressed against an artery of the subject via a skin of the subject, said pressure pulse wave sensor detecting, as said second pulse wave, a pressure pulse wave including a plurality of pulses produced from the artery of the subject in synchronism with the heartbeat of the subject.

7. An apparatus according to claim 1, further comprising a display device which displays, along a time axis, a time-wise trend of respective values of said peripheral blood-flow resistance determined by said peripheral blood-flow resistance determining means.

8. An apparatus according to claim 1, wherein said phase-difference determining means comprises means for determining a phase difference of each of heartbeat-synchronous pulses of said first pulse wave and a corresponding one of heartbeat-synchronous pulses of said second pulse wave, and wherein said peripheral blood-flow resistance determining means successively determines, according to said predetermined relationship, a peripheral blood-flow resistance of the subject, based on the phase difference of said each heartbeat-synchronous pulse of said first pulse wave and said corresponding heartbeat-synchronous pulse of said second pulse wave.

9. An apparatus for monitoring a peripheral blood-flow condition of a living subject by detecting a peripheral blood-flow resistance of the subject, comprising:

a first and a second pulse-wave sensor which are adapted to be worn on a first and a second portion of the subject, respectively, to detect a first and a second pulse wave, respectively, each of which is produced in synchronism with a heartbeat of the subject;

phase-difference determining means for determining a difference of respective phases of said first and second pulse waves detected by said first and second pulse-wave sensors;

peripheral blood-flow resistance determining means for determining said peripheral blood-flow resistance of the subject, based on the phase difference determined by said phase-difference determining means, according to a predetermined relationship between peripheral blood-flow resistance and phase difference; and index-value determining means for determining an index value indicative of a characteristic of a waveform of a decreasing portion of a heartbeat-synchronous pulse of said second pulse wave detected by said second pulse-wave sensor, wherein said peripheral blood-flow resistance determining means comprises correcting means for correcting, based on said index value determined by said index-value determining means, said peripheral blood-flow resistance determined based on said phase difference determined by said phase-difference determining means.

10. An apparatus according to claim 9, wherein said second pulse-wave sensor comprises a pressure pulse wave sensor adapted to be pressed against an artery of the subject via a skin of the subject, said pressure pulse wave sensor detecting, as said second pulse wave, a pressure pulse wave including a plurality of pulses produced from the artery of the subject in synchronism with the heartbeat of the subject.

11. An apparatus according to claim 9, further comprising a display device which displays, along a time axis, a time-wise trend of respective corrected values of said peripheral blood-flow resistance which are provided by said correcting means of said peripheral blood-flow resistance determining means.

12. An apparatus according to claim 9, wherein said phase-difference determining means comprises means for determining a phase difference of each of heartbeat-synchronous pulses of said first pulse wave and a corresponding one of heartbeat-synchronous pulses of said second pulse wave, and wherein said peripheral blood-flow resistance determining means comprises means for determining, according to said predetermined relationship, a peripheral blood-flow resistance of the subject, based on the phase difference of said each heartbeat-synchronous pulse of said first pulse wave and said corresponding heartbeat-synchronous pulse of said second pulse wave.

* * * * *